In vitro method for developing dendritic Langerhans type cells, for use in immunotherapy against cancer or infectious diseases and enhancement of graft survival in mammals. The method includes the steps of: culturing cells selected from peripheral blood monocytes and bone marrow cells in a medium containing platelets obtained from the same species or phylogenetically close species; and incubating the culture at 30 to 40° C. for a period sufficient to enable formation of mature dendritic Langerhans type cells.

(12) United States Patent
Bandyopadhyay et al.

(10) Patent No.: US 7,638,329 B2
(45) Date of Patent: Dec. 29, 2009

(54) IN VITRO METHOD TO GENERATE DENDRITIC LANGERHANS TYPE CELLS

(75) Inventors: Santu Bandyopadhyay, Calcutta (IN); Keshab Chandra Roy, Calcutta (IN); Monidipa Gosh, Calcutta (IN); Mitali Ray, Calcutta (IN); Chiranjib Pal, Calcutta (IN); Samir Bhattacharya, Calcutta (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/800,448

(22) Filed: Mar. 5, 2001

(65) Prior Publication Data

US 2002/0123140 A1 Sep. 5, 2002

(51) Int. Cl.
*C12N 5/00* (2006.01)
*C12N 5/02* (2006.01)

(52) U.S. Cl. .................... 435/377; 435/383

(58) Field of Classification Search ................ 435/355, 435/372, 375, 377, 383
See application file for complete search history.

(56) References Cited

U.S. PATENT DOCUMENTS 6,828,157 B1 * 12/2004 Pankowsky ................ 436/176

OTHER PUBLICATIONS

Steinman, R. Dendritic Cells, in Fundamental Immunology. Paul, W., ed. 1999;p. 523.*
Williams et al. Isolation and Function of Human DCs, in International Review Cytology. 1994; vol. 153, pp. 54-57.*
Caux et al. J. Exp. Med. 1996; vol. 184, pp. 695-706.*
Semple, J.W., et al. Blood, Nov. 15, 1991; 78(10):2619-2625.*
Bone Marrow, www.wikepedia.org.*
Brand, C.U., et al. Arch. Dermatol. Res. 1999;291:65-72.*
Romani. N., et al. AMPIS. 2003;111:725-740.*
PathologyOutlines internet site, outline/chapter entitled "CD Markers", entry: CD83, last visited Jul. 22, 2003.
Schoppet M et al., 2003, "CD83+ dendritic cells in inflammatory infiltrates of Churg-Strauss myocarditis", *Arch Pathol Lab Med.* 127:98-101.
Geissmann F et al., 2001, "Differentiation of Langerhans cells in Langerhans cell histiocytosis", *Blood* 97:1241-1248.
Satthaporn S et al., 2001, "Dendritic cells (I): Biological functions", *J R Coll Surg Edinb.* 46: 9-19.
Hirano A et al., 2000, "Graft hyporeactivity induced by donor-derived dendritic cell progenitors", *Transplant Proc.* 32:260-264.
Chakraborty NG et al., 1999, "Emergence of regulatory CD4+ T cell response to repetitive stimulation with antigen-presenting cells in vitro: implications in designing antigen-presenting cell-based tumor vaccines", *J. Immunol.* 162:5576-5583.
Dhodapkar MV et al., 1999, "Rapid generation of broad T-cell immunity in humans after a single injection of mature dendritic cells", *J. Clin. Invest.* 104:173-180.
Banchereau J et al., 1998, "Dendritic cells and the control of immunity", *Nature* 392(6673):245-252.
Khanna A et al., 1998, "Donor bone marrow potentiates the effect of tacrolimus on nonvascularized heart allograft survival: association with microchimerism and growth of donor dendritic cell progenitors from recipient bone marrow", *Transplantation* 65:479-485.*
Palucka KA et al., 1998, "Dendritic cells as the terminal stage of monocyte differentiation", *J. Immunol.* 160:4587-4595.*
Hsu FJ et al., 1996, "Vaccination of patients with B-cell lymphoma using autologous antigen-pulsed dendritic cells", *Nature Medicine* 2:52-58.*
Young JW et al., 1996, "Dendritic cells as adjuvants for class I major histocompatibility complex-restricted antitumor immunity", *J. Exp. Med.* 183:7-11.*
Caux C et al., 1992, "GM-CSF and TNF-alpha cooperate in the generation of dendritic Langerhan cells", *Nature* 360:258-261.*
Steinman RM et al., 1974, "Identification of a novel cell type in peripheral lymphoid organs of mice. 3. Functional properties in vivo", *J. Exp. Med.* 139:1431-1445; and.*
Steinman et al., 1973, "Identification of a novel cell type in peripheral lymphoid organs of mice. I Morphology, quantitation, tissue distribution" *J. Exp. Med.* 137:1142-1162.*

* cited by examiner

*Primary Examiner*—G. R Ewoldt
(74) *Attorney, Agent, or Firm*—Baker Botts LLP

(57) ABSTRACT

Described is an in vitro method for developing dendritic Langerhans type cells, for use in immunotherapy against cancer or infectious diseases and enhancement of graft survival in mammals. The method includes the steps of: culturing cells selected from peripheral blood monocytes and bone marrow cells in a medium containing platelets obtained from the same species or phylogenetically close species; and incubating the culture at 30 to 40° C. for a period sufficient to enable formation of mature dendritic Langerhans type cells.

13 Claims, 3 Drawing Sheets

IN VITRO METHOD TO GENERATE DENDRITIC LANGERHANS TYPE CELLS

FIELD OF THE INVENTION

Figure 1:
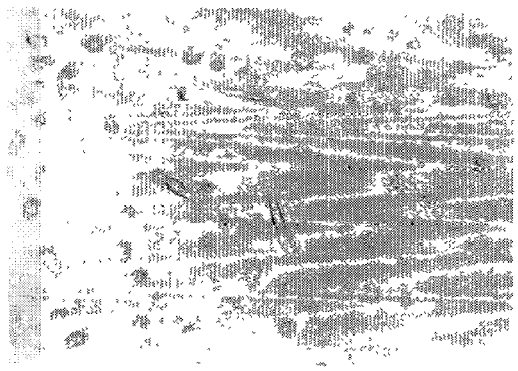
Figure 1:
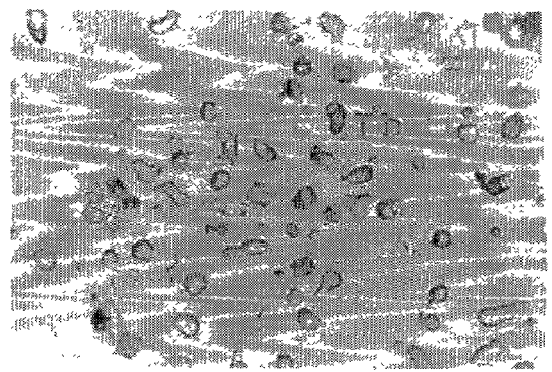
Figure 1:
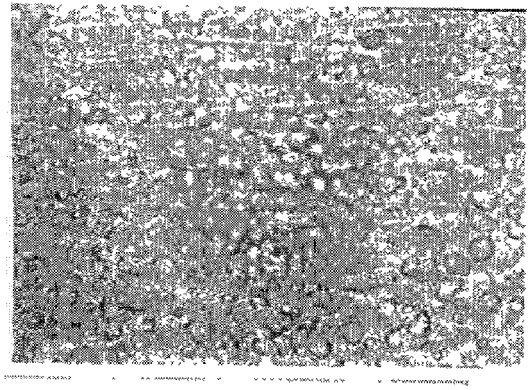
Figure 1:
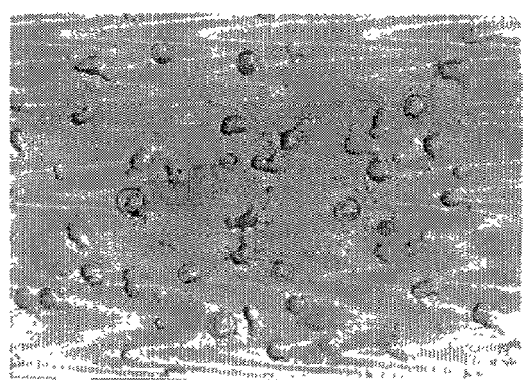

The present invention relates to a novel in vitro method for the generation of dendritic Langerhans type cells from peripheral blood monocytes especially the platelets.

BACKGROUND AND PRIOR ART REFERENCES

Dendritic cells (DC), first described by Steinman and Cohn, Z. A. J. Exp. Med. 137: 1142, 1973 are the most potent antigen presenting cells which initiate immune responses such as the sensitization of T cells restricted by major histocompatibility complex molecules, the rejection of organ transplants and the formation of T cell dependent antibodies. They differentiate from their precursors into so-called "immature" DCs which are present in most tissues (Banchereau, J. and Steinman, R. M. Nature 392: 245, 1998). The best characterized immature DCs is the Langerhans cells (LC), located above the basal layer of epithelial cells of the skin. Until recently, it was difficult to isolate dendritic cells or Langerhans cells (Steinman, R. M., Lustig, D. S. and Cohn, Z. A. J. Exp. Med. 139: 1431, 1974). Our knowledge on these important antigen presenting cells has increased dramatically because of success in culturing these cells in vitro. Granulocyte macrophage colony stimulating factor (GM-CSF) and interleukin-4 (IL-4) favours the outgrowth of dendritic cells from $CD14^+$ blood monocytes and $CD34^+$ cord blood stem cells (Palucka, K. A. Taquet, N. Sanchezchapuis, F. and Gluckman, J. C. J. Immunol. 160: 4587, 1998). On the other hand, transforming growth factor β1 (TGF β1) and IL-4, induces differentiation of human peripheral blood monocytes into dendritic Langerhans cells (Geissmann, F. C., Prost, J., Monnet, M., Dy, M., Browsse, N. and Hermine, O. J. Exp. Med. 187: 961, 1998). Culturing purified cord blood $CD34^+$ cells with GM-CSF and tumor necrosis factor α (TNF-α) also leads to dendritic Langerhans cells (Caux, C., Dezutter-Dambuyant, C., Schmitt, D. and Banchereau, J. Nature 360: 258, 1992).

Several studies have shown that in vitro grown dendritic cells or dendritic Langerhans cells can be used in active, specific vaccination schemes to generate protective immunity in several tumour models (Young, J. W. and Inaba, K. J. Exp. Med. 187: 7, 1996). (Chakraborty, N. G., Li, L., Sporn, J. R., Kurtzman, S. H., Ergin, M. T. and Mukheji, B. J. Immunol. 162: 5576, 1991; Hsu, F. J., Benike, C., Fagnoni, F., Liles, T. M., Czerwinski, D., Taidi, B., Engleman, E. G. and Ltry, R. Nature Medicine 2: 52, 1996). Controlled studies confirmed the immunogenecity of in vitro grown DCs in human, and demonstrated that a single injection of mature DCs rapidly expands T cell immunity (Dhodapkar, M. V., Steinman, R. M., Sapp, M., Desai, H., Fossella, C., Krasrvsky, J., Donahoe, S. M., Dunbar, P. R., Cerundolo, V., Nixon, D. F. and Bhardwaj, N. J. Clin. Invest. 104: 173, 1999).

Evidences are being accumulated on the potential of dendritic Langerhans cells in enhancing organ transplant survival. Graft hyporeactivity induced by donor derived dendritic cell progenitors has been reported in animal model (Hirano, A., Fraser, M. O., Jordan, M. L., Takayama, T., Lu, L. and Thomson, A. W. Transplant Proc. 32: 260, 2000). This is associated with microchiemerism and growth of donor dendritic cell progenitors in recipient bone marrow (Khanna, A., Steptae, R. J., Antonysamy, M. A., Li, S. and Thomson, A. W. Transplantation 65: 479, 1998).

OBJECT OF THE INVENTION

The main object of the invention is to provide a novel method to generate dendritic Langerhans type cells in vitro using platelets.

Another object of the invention is to provide a novel method to generate human dendritic Langerhans type cells in vitro from human peripheral blood monocytes using human platelets.

Another object of the invention is to provide a novel method to generate animal dendritic Langerhans type cells from animal bone marrow cells using animal platelets.

Yet another object of the invention is to provide novel method to generate dendritic Langerhans type cells in vitro from any mammalian species from their peripheral blood monocytes or bone marrow cells using platelets of the same species or from a phylogenetically close species.

SUMMARY OF THE INVENTION

The invention provides an in vitro method for developing dendritic Langerhans type cells, for use in immunotherapy against cancer or infectious diseases and enhancement of graft survival in mammals, said method comprising the steps of: culturing cells selected from peripheral blood monocytes and bone marrow cells in a medium containing platelets obtained from the same species or phylogenetically close species and incubating the culture at 30 to 40° C. for a period sufficient to enable formation of mature dendritic Langerhans type cells. Using this novel strategy dendritic Langerhans type cells are generated from any mammalian species from their peripheral blood monocytes or bone marrow cells using platelets of the same species or phylogenetically close species. These cells are useful for immunotherapy against cancers or infectious diseases and enhancement of graft survival. Particularly, the present invention involves a novel strategy to generate dendritic Langerhans type cells without the addition of (i.e., omits) exogenous cytokines.

DETAILED DESCRIPTION OF THE INVENTION

The invention provides an in vitro method for developing dendritic Langerhans type cells, for use in immunotherapy against cancer or infectious diseases and enhancement of graft survival in mammals, said method comprising the steps of:

a. culturing cells selected from peripheral blood monocytes and bone marrow cells in a medium containing platelets obtained from the same species or phylogenetically close species; and b. incubating the culture at 30 to 40° C. for a period sufficient to enable formation of mature dendritic Langerhans type cells.

In an embodiment of the invention, the culture is incubated at about 30° C. to about 40° C.

In an embodiment, the medium comprises RPMI-1640

In yet another embodiment, the cells are cultured for a period of 2 to 8 days.

In still another embodiment, fetal calf serum is added to the medium, with at least 2% being preferable.

In an embodiment, human platelets are added to the medium to develop dendritic Langerhans type cells.

In yet another embodiment, rat platelets are added to the medium containing mice blood cells to develop dendritic Langerhans type cells.

Further, the method to generate human dendritic Langerhans type cells in vitro from human peripheral blood monocytes uses human platelets wherein the said method comprises the following steps:

a. preparing human peripheral blood monocytes;
b. preparing human platelets;
c. culturing human peripheral blood monocytes with human platelets for in vitro generation of human dendritic Langerhans type cells;
d. morphological analysis of in vitro generated human dendritic Langerhans type cells; and
e. flow cytometric analysis of in vitro generated human dendritic Langerhans type cells.

In another embodiment the method for generation of mouse dendritic Langerhans type cells, comprises the following steps:

a. preparing mouse bone marrow cells;
b. culturing of rat platelets;
c. in vitro generation of mouse dendritic Langerhans type cells by culturing mouse bone marrow cells with rat platelets; and
d. morphological analysis of in vitro generated mouse dendritic Langerhans type cells.

One more embodiment, relates to a method to generate dendritic Langerhans type cells from any mammalian species using platelets wherein the said method comprises the following steps:

a. preparing peripheral blood monocytes and or bone marrow cells;
b. culturing peripheral blood monocytes or bone marrow cells with platelets of the same species or phylogenetically close species for in vitro generation of dendritic Langerhans type cells;
c. morphological analysis of the in vitro generated dendritic Langerhans type cells; and
d. flow cytometric analysis of the in vitro generated dendritic Langerhans type cells.

In another embodiment of the invention, the method for producing dendritic Langerhans cells comprises culturing cells in a medium that omits an exogenous cytokine. The cytokine may be granulocyte macrophage colony stimulating factor or interleukin-4.

In an embodiment of the invention, the medium contains about at least about 2% fetal calf serum. In an alternative embodiment, the medium contains about 10% fetal calf serum.

In another embodiment of the invention, the cells are cultured for a period of about 2 to about 8 days.

In another embodiment of the invention, human platelets are added to the medium to produce human dendritic Langerhans cells from human monocyte or bone marrow cells. Alternatively, the platelets and the peripheral blood monocytes and/or bone marrow cells are selected from phylogenetically close species. For example, rat platelet cells may be added to a medium containing mice blood cells.

BRIEF DESCRIPTION OF THE ACCOMPANYING DRAWINGS

FIG. 1. Comparison of morphology of human dendritic Langerhans type cells grown in vitro from human peripheral blood monocytes using human platelets or recombinant cytokines. Ten days cultures are shown. Magnification, ×300.

A. Medium RPMI only (without FCS);
B. Medium RPMI without FCS+ Platelets;
C. Medium RPMI containing 2% FCS+rhGMCSF+rhIL-4
D. Medium RPMI containing 2% FCS+ Platelets FIG. 2. Immunophenotyping of human dendritic Langerhans type cells generated in vitro from human peripheral blood monocytes using human platelets. One colour dotplot is shown. The percent positive cells are given in the upper left or lower right quadrants.

Figure 3:
Figure 3:
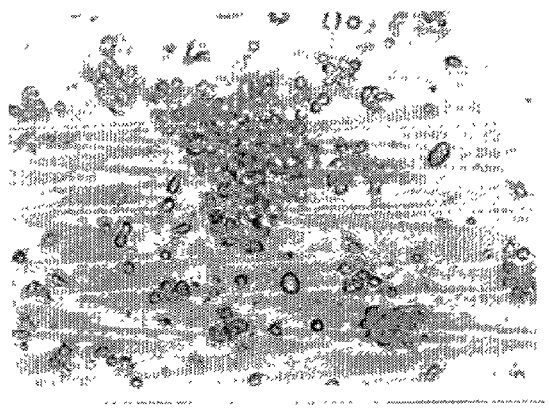

FIG. 3. Mouse dendritic Langerhans type cells generated in vitro from mouse bone marrow using rat platelets. BALB/c mice bone marrow cells ($300 \times 10^3$/well) were cultured in RPMI-1640 containing 10% FCS with or without rat (SpragueDowley) platelets ($2 \times 10^8$/ml) in 24 well tissue culture plates. Phase contrast micrographs of five days cultures are shown. Magnification, ×300.

A. Medium RPMI containing 10% FCS; and
B. Medium RPMI containing 10% FCS+ rat platelets The invention is illustrated by the following examples which should not be construed as limitations on the inventive scope embodied herein.

EXAMPLE 1

Preparation of Human Blood Monocytes

Heparinised (10 U/ml) normal human whole blood was subjected to Ficoll/Hypaque density gradient centrifugation to get peripheral blood mononuclear cells (PBMC). PBMC were washed (×5) in RPMI-1640 medium without fetal calf serum (FCS). PBMC were then allowed to adhere in 24 Well tissue culture plates ($1.5 \times 10^6$ cells/well) for three hours. Non-adherent cells were removed by gentle swirling followed by washing (×3). Adherent monocytes were cultured at 37° C. in 5% $CO_2$ with or without human platelets. Recombinant human granulocyte macrophage colony stimulating factor (rhGM-CSF) and recombinant human interleukin-4 (rhIL-4) were added in parallel cultures for comparison purpose.

EXAMPLE 2

Preparation of Human Platelets

Heparinised human whole blood was centrifuged for 15 mins at 2000 rpm to pellet down the RBC, mononuclear cells (PBMC) and Polymorphonuclear neutrophils (PMN). The plasma containing the platelets was collected and the centrifugation was repeated to remove any residual RBC, PBMC and PMN. The plasma was then subjected to high speed centrifugation (10,000 rpm for 10 min) to pellet down the platelets. The platelets were washed (×2 with RPMI-1640 without FCS) and counted.

EXAMPLE 3

In Vitro Generation of Human Dendritic Langerhans Type Cells by Incubating Human Blood Monocytes with Human Platelets.

Adherent monocytes were cultured in RPMI-1640 (without FCS) in the presence or absence of human platelets ($2 \times 10^8$/ml of culture) at 37° C. in 5% $CO_2$. In selected experiments, RPMI-1640 containing 2% FCS was also used instead of RPMI-1640 without FCS. No medium change was done. Cells were kept in the same wells for up to 60 days with >95% viability.

EXAMPLE 4

Generation of Mouse Dendritic Langerhans Type Cells in Vitro from Mouse Bone Marrow Using Rat Platelets BALB/c mice bone marrow cells ($30 \times 10^5$ cells/well) were cultured in RPMI-1640 medium containing 10% FCS in 24 well plates. Rat platelets were prepared from rat plasma and added ($2 \times 10^8$ cells/ml) to mouse bone marrow cultures. Cultures were incubated at 37° C. in 5% $CO_2$. Rat platelets were prepared from the whole heparinised blood of Sprague-Dowley rats using the same method as for human platelets.

EXAMPLE 5

Morphological Analysis

In vitro generated human and mouse dendritic Langerhans type cells were analysed under phase contrast microscope.

EXAMPLE 6

Flow Cytometry

Immunophenotyping of in vitro generated human dendritic Langerhans type cells was performed by flow cytometry using FACS Calibur (Becton Dickinson, USA) flow cytometer, and the following human cell surface marker specific monoclonal antibodies (mAb): anti-CD3, anti-HLADR, anti-CD19, anti-CD40, anti-CD1a, anti-CD1b, antiCD80, anti-CD83 and anti-CD86 (purchased from Pharmingen, USA).

Results

Human Platelets Induce Generation of Dendritic Langerhans Type Cells in Vitro from Human Peripheral Monocytes When human peripheral blood monocytes were cultured in RPMI-1640 medium without FCS, very few cells differentiated to strongly adherent macrophages and most of the cells died (FIG. 1A). When human monocytes were cultured in RPMI-1640 without FCS in the presence of rhGM-CSF and rhIL-4, there was hardly any transformation to immature DC with typical dendritic processes (not shown). However, when human peripheral blood monocytes were cultured in RPMI-1640 containing 2% FCS in the presence of 500 U/ml of rhGM-CSF and 500 U/ml of rhIL-4, transformation to immature dendritic cells (DC) with typical dendritic processes was noticed, as expected (FIG. 1C). In parallel cultures of human monocytes in FCS free medium when autologous platelets were added instead of rhGM-CSF and rhIL-4 proliferating cells with dendritic processes started appearing within five to six days. FIG. 1B shows growing colonies that developed when autologous platelets were added to serum-free human monocyte cultures. Morphologically these cells were similar to that generated in the presence of rhGM-CSF and rhIL-4. Of course, the presence of 2% FCS in human monocyte cultures containing autologous platelets accelerated the process of colony formation of cells with typical dendritic morphology. Typical dendritic processes of these cells grown in RPMI-1640 containing 2% FCS and autologous platelets are shown in FIG. 1D. Platelets collected from allogeneic donors were as effective as autologous platelets in inducing growth of cells with dendritic processes from human monocytes.

Figure 2:
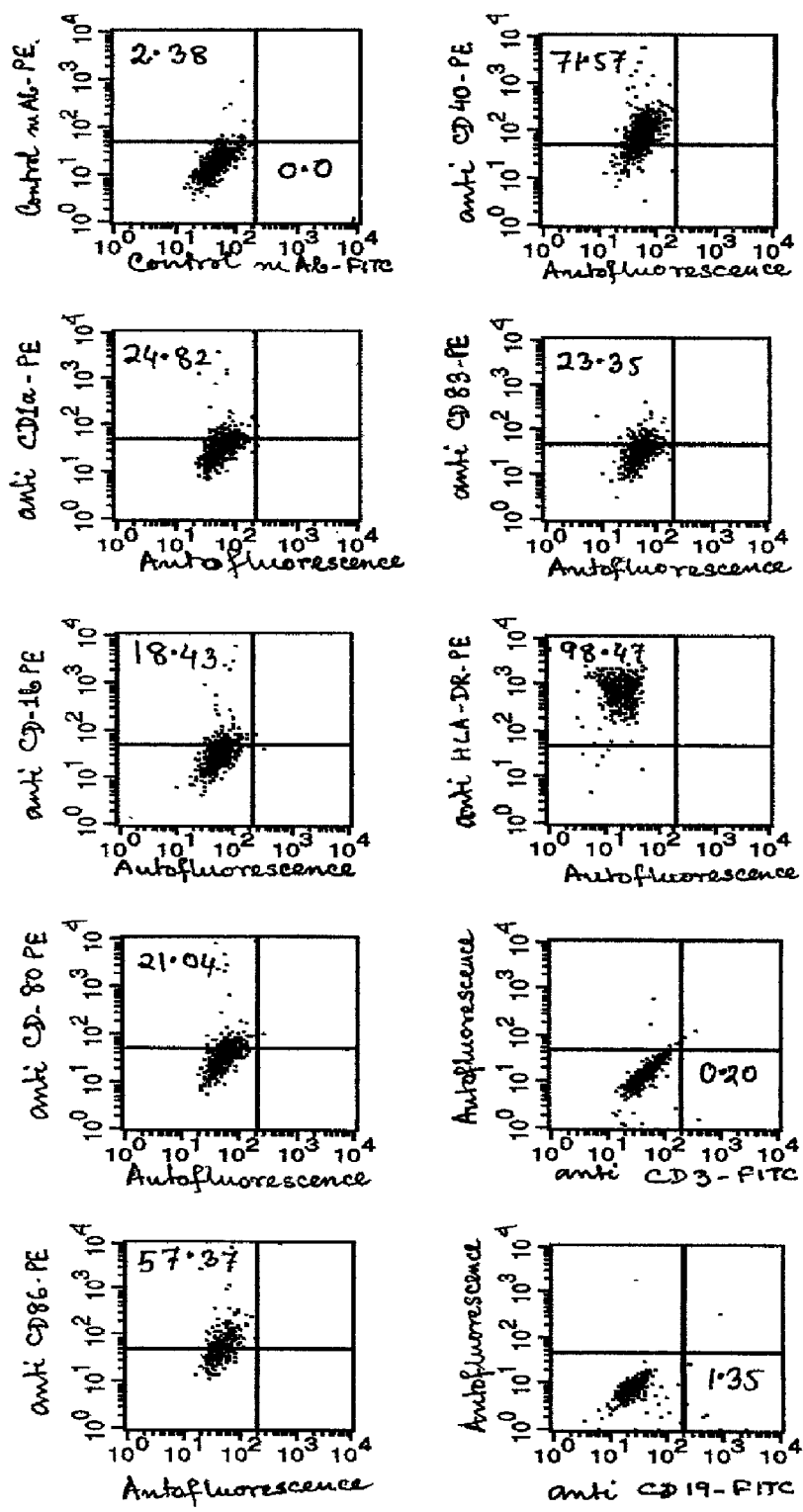

Immunophenotyping of these cells ruled out the possibility of contaminating T or B cells as $CD3^+$ and $CD19^+$ cells in these cultures were 0.2% and 1.35% respectively (FIG. 2). The cells showed strong reactivity with anti-HLA-DR, anti-CD40 and anti-CD86 mAbs. The reactivity with anti-HLA-DR, anti-CD40 and anti-CD86 were 98.4%, 71.5% and 57.3% respectively. However, only approximately 20% of the cells expressed CD1a, CD1b, CD80 or CD83 (FIG. 2). Taken together, these data suggest that the growing cells with typical dendritic morphology that were generated when human monocytes were cultured in the presence of autologous platelets are dendritic Langerhans type cells.

Rat Platelets Induce Generation of Mouse Dendritic Langerhans Type Cells in Vitro from Mouse Bone Marrow To extend our finding in animal models, BALB/c mice bone marrow cells were cultured in RPMI-1640 medium containing 10% FCS and 50 µM β-mercaptoethanol in the presence or absence of human platelets. Human platelets did not induce growth of cells with dendritic morphology from mouse bone marrow (not shown). However, when mouse bone marrow cells were cultured in the same medium in the presence of recombinant mouse granulocyte macrophage colony stimulating factor (rmGM-CSF), cells with dendritic morphology started growing, as expected (not shown). Interestingly, when platelets collected from Sprague-Dowley rat plasma were added to mouse bone marrow cell cultures in RPMI-1640 containing 10% FCS and 50 µM β-mercaptoethanol, growing colonies with dendritic morphology started appearing from five days of incubation (FIG. 3B). When mouse bone marrow cells were cultured in the absence of rmGM-CSF or rat platelets no such colonies with dendritic morphology were seen, only some adherent macrophages were visible (FIG. 3A). Our data indicate that platelets from autologous or allogeneic normal human donors can generate dendritic Langerhans type cells from human peripheral blood monocytes in vitro. Although human platelets were ineffective in generating dendritic Langerhans type cells from mouse bone marrow, platelets from rats could induce the same. This is possibly because rat is phylogenetically more close to mouse than human. Thus, dendritic Langerhans type cells could be generated from any mammalian species from their peripheral blood monocytes or bone marrow cells using platelets of the same species or phylogenetically close species without the addition of any exogenous cytokines.

Application

In vitro generated dendritic Langerhans type cells from human peripheral blood monocytes using human platelets may have potential application in immunotherapy against human cancers or infectious diseases. Another potential application is in enhancement of organ transplant survival by inducing donor graft-specific tolerance. In vitro generated dendritic Langerhans type cells from animals may be useful in developing immunotherapeutic strategies for cancer and infectious diseases in animal models. These cells may also prove useful in studying tolerance in animal models.

Advantage

The conventional method of generating dendritic Langerhans type cells in vitro requires addition of recombinant cytokines like GM-CSF, IL-4 and TGF-β1 to peripheral blood monocyte or bone marrow cultures. These cytokines are expensive. Therefore, generation of dendritic Langerhans cells in vitro using the conventional method is costly. On the other hand, our novel method of generating dendritic Langerhans type cells does not require the addition of any exogenous cytokines to monocyte or bone marrow cultures. Only platelets collected from the same species or from a phylogenetically close species can replace the requirement of exogenous cytokines. Platelets are easy to get and are inexpensive to prepare. Using this novel method large number of dendritic Langerhans type cells are generated in vitro very easily and inexpensively from any mammalian species including human.

The human dendritic Langerhans type cells generated in vitro following the method of the invention is useful for immunotherapy against human cancers and infectious diseases. The human dendritic Langerhans type cells generated in vitro is effective in enhancing survival of organ transplants in human. In vitro generated dendritic Langerhans type cells from animals may be useful in developing immunotherapeutic strategies for cancer and infectious diseases in animal models. In vitro generated dendritic Langerhans type cells from animals may be useful in studying tolerance in animal models.

The invention claimed is:

1. An in vitro method for generating mammalian dendritic Langerhans type cells, said method comprising:
   a. culturing cells selected from the group consisting of peripheral blood monocytes and bone marrow cells from a mammalian species in a medium containing platelets obtained from the same species;
   b. incubating the culture at 30° C. to 40° C. for a period sufficient to enable in vitro generation of dendritic Langerhans type cells,
   c. performing a morphological analysis of the in vitro generated dendritic Langerhans type cells; and
   d. performing flow cytometric analysis of the in vitro generated dendritic Langerhans type cells.

2. The method of claim 1 wherein the medium omits an exogenous cytokine.

3. The method of claim 1 wherein the medium comprises RPMI-1640.

4. The method of claim 1 wherein the cells are cultured for a period of 2 to 8 days.

5. The method of claim 1 wherein the medium further comprises at least 2 percent fetal calf serum.

6. The method of claim 1 wherein the mammalian species is human.

7. An in vitro method for generating human dendritic Langerhans type cells, said method comprising:
   a. culturing human peripheral blood monocytes in a medium containing human platelets;
   b. incubating the culture at 30° C. to 40° C. for a period sufficient to enable in vitro generation of human dendritic Langerhans type cells,
   c. performing a morphological analysis of the in vitro generated dendritic Langerhans type cells; and
   d. performing flow cytometric analysis of the in vitro generated dendritic Langerhans type cells.

8. The method of claim 7 wherein the medium omits an exogenous cytokine.

9. The method of claim 7 wherein the medium comprises RPMI-1640.

10. The method of claim 7 wherein the cells are cultured for a period of 2 to 8 days.

11. The method of claim 7 wherein the medium further comprises at least 2 percent fetal calf serum.

12. The method of claim 6, wherein the flow cytometric analysis comprises immunophenotyping the in vitro generated dendritic Langerhans type cells by using a monoclonal antibody specific for a human cell surface marker, wherein the antibody is selected from anti-CD3, anti-HLADR, anti-CD19, anti-CD40, anti-CD1a, anti-CD1b, anti-CD80, anti-CD83 and anti-CD86.

13. The method of claim 7, wherein the flow cytometric analysis comprises using a monoclonal antibody specific for a human cell surface marker, wherein the antibody is selected from anti-CD3, anti-HLADR, anti-CD19, anti-CD40, anti-CD1a, anti-CD1b, anti-CD80, anti-CD83 and anti-CD86.

* * * * *